United States Patent [19]
Fabry et al.

[11] Patent Number: 5,391,786
[45] Date of Patent: Feb. 21, 1995

[54] PROCESS FOR THE PRODUCTION OF LIGHT-COLORED WASHING-ACTIVE α-SULFOFATTY ACID LOWER ALKYL ESTER SALTS

[75] Inventors: Bernd Fabry, Korschenbroich; Ulrich Kratzel, Kulmbach; Wolfgang Schmidt, Monheim; Guenter Kreienfeld, Duesseldorf, all of Germany

[73] Assignee: Henkel Kommanditgesellschaft auf Aktien, Duesseldorf, Germany

[21] Appl. No.: 937,897

[22] PCT Filed: Apr. 5, 1991

[86] PCT No.: PCT/EP91/00644
§ 371 Date: Oct. 14, 1992
§ 102(e) Date: Oct. 14, 1992

[87] PCT Pub. No.: WO91/16300
PCT Pub. Date: Oct. 31, 1991

[30] Foreign Application Priority Data

Apr. 14, 1990 [DE] Germany ............... 4012106

[51] Int. Cl.$^6$ ............................................. C07C 51/36
[52] U.S. Cl. ..................... 554/145; 554/97; 554/98; 554/141; 554/190; 554/191
[58] Field of Search .............. 554/97, 98, 190, 191, 554/141, 145

[56] References Cited

U.S. PATENT DOCUMENTS 4,547,318 10/1985 Kloetzer et al. ............... 260/400
4,671,900 6/1987 Schmid et al. ................. 260/400
4,820,451 4/1989 Piorr et al. ..................... 260/400

FOREIGN PATENT DOCUMENTS 0222237 5/1987 European Pat. Off. .
1443995 1/1970 Germany .
3319591 12/1984 Germany .

OTHER PUBLICATIONS

Journal of American Oil Chem. Soc., 39, 1962, pp. 490–495.
Fat Science Technology, 89, 1987, pp. 237–248.

*Primary Examiner*—José G. Dees
*Assistant Examiner*—D. D. Carr
*Attorney, Agent, or Firm*—Wayne C. Jaeschke; John E. Drach; Henry E. Millson, Jr.

[57] ABSTRACT

Light-colored ester sulfonates can be obtained by sulfonation of fatty acid lower alkyl esters and subsequent working up providing fatty acid esters having a low content of oxo compounds and unsaturated compounds are used in the sulfonation stage.

20 Claims, No Drawings

PROCESS FOR THE PRODUCTION OF LIGHT-COLORED WASHING-ACTIVE α-SULFOFATTY ACID LOWER ALKYL ESTER SALTS

BACKGROUND OF THE INVENTION

1. Field of the Invention

This invention relates to a process for the production of light-colored washing active α-sulfofatty acid lower alkyl ester salts by pretreatment of fatty acid lower alkyl esters, reaction with gaseous sulfur trioxide and subsequent working up.

2. Statement of Related Art

The sulfonation of fatty acid lower alkyl esters for the production of α-sulfofatty acid lower alkyl ester salts (hereinafter referred to as "ester sulfonates") has been known for some time (J.Am.Oil.Chem.Soc. 39, 490 (1962)). On an industrial scale, the starting materials used are fats and/or oils of vegetable or animal origin from which the fatty acid lower alkyl esters are obtained either by lipolysis and subsequent esterification with lower alcohols or by transesterification of the natural triglycerides with lower alcohols. Depending on the origin of the natural raw material, the fatty acid ester mixtures obtained contain esters of $C_{6-22}$ fatty acids. Technical fatty acid lower alkyl ester such as these are sulfonated with gaseous sulfur trioxide by known methods which are described, for example, in German patent applications DE-A-12 48 645 and DE-A-11 79 931. This leads to more or less heavily discolored acidic crude products which are bleached and converted into the corresponding α-sulfofatty acid lower alkyl ester salts by neutralization at pH 6 to 7. In this form, the ester sulfonates have acquired considerable significance as surfactants for the production of detergents and cleaning preparations.

Despite optimal sulfonation conditions, however, dark-colored products are frequently obtained in the production of ester sulfonates and cannot be lightened in color sufficiently, if at all, by conventional bleaching methods. Products regarded as critical in this regard have a Klett color value after bleaching (as determined in a 1 cm round cuvette at a concentration of 5% by weight washing-active substance in water) above 30. Ester sulfonates of this type are unsuitable for the production of detergents and cleaning preparations on aesthetic grounds.

There has been no shortage of attempts in the past to develop processes by which light-colored ester sulfonates could be produced.

According to the teaching of German patent application DE-A-12 46 718, it is essential for the production of light-colored ester sulfonates to use only those fatty acid esters in which the content of unsaturated compounds does not exceed 0.1 to 0.5% by weight for the sulfonation step. In practice, however, it has been found that even fatty acid lower alkyl esters containing 0.1 to 0.3% by weight unsaturated compounds can give rise to ester sulfonates of unsatisfactory color quality.

According to DE-C-12 62 265, mixtures of fatty acid lower alkyl esters and at least 25% by weight of an alkyl benzene are together reacted with sulfur trioxide with a view to improving color quality. However, it is only possible by this method to obtain mixtures of anionic surfactants which contain alkyl benzenesulfonates in addition to ester sulfonates.

DE-A-14 43 995 shows that ester sulfonates of good color quality can be obtained by limiting the degree of sulfonation to around 90%. However, ester sulfonates having a low degree of sulfonation lead to problems in the manufacture of powder-form detergents by spray-drying because experience has shown that the processing of such products is accompanied by intensive pluming.

Finally, EP-B-0 054 724 describes a process for the production of light-colored ester sulfonates in which fatty acid esters of which the fatty acid glyceride content has been reduced by distillation to values of 0.3 to 0.5% by weight are used for the sulfonation step. In practice, however, it has been found that this measure is not in itself sufficient to guarantee the production of light-colored ester sulfonates irrespective of the starting material and its pretreatment.

Accordingly, the problem addressed by the invention was to develop an improved process for the production of light-colored washing-active α-sulfofatty acid lower alkyl esters which would not be attended by any of the abovementioned disadvantages.

DESCRIPTION OF THE INVENTION

The present invention relates to a process for the production of light-colored washing-active α-sulfofatty acid lower alkyl ester salts by sulfonation of fatty acid lower alkyl esters with gaseous sulfur trioxide and subsequent working up, characterized in that fatty acid lower alkyl esters a) in which the content of oxo compounds has been reduced to values below 0.1% by weight and
b) in which the content of unsaturated compounds has been reduced to values below 0.1% by weight (percentages by weight based on fatty acid lower alkyl ester) are introduced into the sulfonation stage.

The invention is based on the observation that the content of oxo compounds and unsaturated compounds in the fatty acid lower alkyl ester is of primary importance in regard to the formation of dark-colored ester sulfonates. The invention also includes the observation that the compounds mentioned influence one another in their color-deteriorating effect and that only measures aimed at reducing the contents of both groups of color promoters are appropriate for guaranteeing the production of light-colored ester sulfonates.

For the production of light-colored ester sulfonates, fatty acid lower alkyl esters in which the content of oxo compounds has been reduced to values below 0.1% by weight and preferably to values below 0.05% by weight, based on the fatty acid lower alkyl ester, by a1) distillation in the presence of inorganic acids or partial esters thereof with glycerol and/or
a2) adsorption to inorganic solids are introduced into the sulfonation stage.

Hydroxy-, dihydroxy- and keto-fatty acid esters which are present as impurities in fatty acid lower alkyl esters through autoxidation of unsaturated fatty acid esters are particularly troublesome oxo compounds. The group of oxo compounds also includes sterol derivatives, such as for example cholesterin or cholesterol, which accompany natural fatty acid esters, particularly of animal origin.

The inorganic acids are introduced into the distillation stage in a concentration of 0.05 to 0.5% by weight, based on the fatty acid lower alkyl ester. Suitable inorganic acids are phosphoric acid, hypophosphorous acid and, in particular, boric acid and also partial esters thereof with glycerol. Distillation may be carried out continuously or discontinuously at a temperature of 230° to 280° C. and under a pressure of 0.05 to 0.2 mbar. The inorganic acid is preferably first introduced into the fatty acid lower alkyl ester at 30° to 40° C. and the mixture is then subjected to overhead distillation in which the inorganic acid and the oxo compounds form esters of low volatility which largely remain at the bottom of the distillation column.

The inorganic solids are introduced into the adsorption stage in a concentration of 10 to 150% by weight and preferably in a concentration of 25 to 100% by weight, based on the fatty acid lower alkyl ester. Suitable inorganic solids are aluminium oxide, titanium dioxide, magnesium oxide and, in particular, silica gel having a particle size of 0.03 to 0.3 mm and preferably 0.06 to 0.2 mm. The inorganic solids are added to the fatty acid lower alkyl ester, the mixture is heated with stirring for 0.5 to 5 h to 40° to 80° C. and preferably to 40° to 70° C. in an inert gas atmosphere and the inorganic solids are then mechanically removed, for example by filtration at 40° to 70° C. The polar oxo compounds adsorb onto the inorganic solids and largely remain in the filtration residue which, after working up, can be returned to the adsorption stage.

In addition, fatty acid lower alkyl esters in which the content of unsaturated compounds has been reduced to values below 0.1% by weight and preferably below 0.05% by weight, based on the fatty acid lower alkyl ester, by hydrogenation in the presence of typical hydrogenation catalysts are introduced into the sulfonation stage for the production of light-colored ester sulfonates.

Particularly troublesome unsaturated compounds are the esters of lower alcohols with unsaturated fatty acids and also fatty acid esters of cholesterol. The hydrogenation reaction may be carried out, for example, using 0.5 to 2% by weight and preferably 0.8 to 1.2% by weight, based on the total quantity of fatty acid ester, of a commercially available nickel catalyst at temperatures of 150° to 220° C. and preferably at temperatures of 170° to 190° C. and under pressures of 5 to 50 bar and preferably 15 to 25 bar. The hydrogenation reaction converts unsaturated fatty acid esters into saturated fatty acid esters.

Esters of $C_{6-22}$ fatty acids with $C_{1-4}$ alcohols, preferably methyl esters of $C_{8-18}$ fatty acids, are used in the sulfonation stage.

The fatty acid esters can be produced by hydrolysis of natural fats and oils and subsequent esterification with lower alcohols or by direct transesterification with lower alcohols.

One preferred embodiment of the invention is characterized by the use of fatty acid lower alkyl esters produced by hydrolysis of natural fats and oils, purification of the resulting fatty acids by the rolling-up process and subsequent esterification with methanol.

Where purification is carried out by the rolling-up process [Fat. Sci. Technol., 89, 237 (1987)], the mixture of saturated and unsaturated fatty acids obtained after hydrolysis is cooled to temperatures of 2° to 7° C., the saturated fatty acids crystallizing and forming a dispersion with the liquid unsaturated fatty acids. By addition of a wetting agent, for example an aqueous solution of a $C_{16-18}$ alkyl sulfate, the unsaturated fatty acids are freed from adhering unsaturated fatty acids. During subsequent centrifugation, this emulsion/dispersion is separated into a phase containing the unsaturated fatty acids, and a dispersion of saturated fatty acids in water which are separated from one another in a separator. The dispersion is then heated to 70° C. and the molten saturated fatty acids are separated from the aqueous phase, the water being returned to the separation process.

The rolling-up process is suitable for reducing the content of unsaturated compounds and certain oxo compounds. According to the invention, a combination of the process steps
1. rolling-up,
2. distillation in the presence of inorganic acids and/or
3. adsorption onto inorganic solids and
4. hydrogenation leads synergistically to particularly light-colored ester sulfonates.

The order in which the above process steps are carried out is of no significance to the successful outcome of the pretreatment according to the invention. However, in order to limit the loss of material during working up, it is advisable to keep to the order indicated.

Sulfonation of the fatty acid lower alkyl esters is carried out by known methods using a mixture of gaseous sulfur trioxide and an inert gas, preferably nitrogen or air, which typically contains 2 to 8% by volume sulfur trioxide. The molar ratio of fatty acid lower alkyl ester to sulfur trioxide is from 1:1.1 to 1:1.8 and preferably from 1:1.2 to 1:1.5. The reaction takes place in a falling-film or cascade reactor at temperatures of 70° to 90° C. On completion of the sulfonation reaction, the acidic reaction mixture obtained is subjected to an afterreaction (ageing) for 10 to 30 minutes and then bleached and neutralized.

Bleaching may be carried out in known manner in aqueous medium with hydrogen peroxide and/or sodium hypochlorite. Neutralization of the acidic reaction product may be carried out both before and after bleaching. Bleaching with hydrogen peroxide before neutralization is described, for example, in DE-B-11 79 931. DE-A-12 34 709 describes a combined bleaching process in which treatment of the acidic reaction product with aqueous hydrogen peroxide is followed by neutralization of the partly bleached sulfonation product, after which a final bleaching process is carried out with hydrogen peroxide or, better still, with sodium hypochlorite. According to DE-A-33 19 591, the crude sulfonation product is first subjected to preliminary bleaching with sodium hypochlorite in a neutral to mildly alkaline aqueous medium, after which the salt paste is mildly acidified and after-bleached with hydrogen peroxide or compounds yielding hydrogen peroxide.

Neutralization of the acidic sulfonation products is carried out with aqueous potassium hydroxide solutions and preferably with aqueous sodium hydroxide solutions. The process conditions under which bleaching and neutralization are carried out should be selected so that saponification of the esters, which would be possible in principle, is largely ruled out.

The following Examples are intended to illustrate the process according to the invention without limiting it in any way.

EXAMPLES

I. Starting esters

Ester I. Tallow fatty acid methyl ester obtained by pressure hydrolysis of beef tallow, thorough removal of unsaturated fatty acids by the rolling-up process and esterification with methanol. The composition and oleochemical data of the ester are shown in Table 1.

Ester II. Tallow fatty acid methyl ester obtained by transesterification of beef tallow with methanol. The composition and oleochemical data of the ester are shown in Table 1.

Ester III. Palm stearin fatty acid methyl ester obtained by pressure hydrolysis of palm oil, substantial removal of unsaturated fatty acids by the rolling-up process and esterification with methanol. The composition and oleochemical data of the ester are shown in Table 1.

TABLE 1

Composition and characteristics data of the esters
Composition data in % by weight

|  | Ester I | Ester II | Ester III |
|---|---|---|---|
| $C_{12}$ fatty acid ester | 2 | 1 | — |
| $C_{14}$ fatty acid ester | 5 | 3 | 4 |
| $C_{16}$ fatty acid ester | 53 | 27 | 79 |
| $C_{18}$ fatty acid ester | 40 | 69 | 17 |
| Oxo compounds | 0.12 | 0.25 | 0.11 |
| Iodine value | 21 | 47 | 21 |
| Hydroxyl value | 1.1 | 1.1 | 1.1 |
| Saponification value | 195.8 | 192.5 | 198.3 |
| Acid value | 0.5 | 0.7 | 0.4 |

II. Pretreatment processes

The fatty acid lower alkyl esters were pretreated by the following process steps:
1. distillation,
2. distillation in the presence of 0.1% by weight boric acid,
3. adsorption using 75% by weight silica gel (Kieselgel 60 ®, grain size 0.063–0.2 mm, Merck), stirring time 3 h, stirring temperature 80° C.,
4. hydrogenation.

Particulars of the processes according to the invention (A–D) and of the comparison processes (E–K) are shown in Table 2:

TABLE 2

| Process | Pretreatment processes | | | | Iodine value |
|---|---|---|---|---|---|
|  | 1. | 2. | 3. | 4. |  |
| A | − | + | − | + | 0.09 |
| B | − | + | − | + | 0.05 |
| C | − | − | + | + | 0.05 |
| D | − | + | + | + | 0.05 |
| E | + | − | − | + | 0.50 |
| F | + | − | − | + | 0.10 |
| G | + | − | − | + | 0.05 |
| H | − | + | − | + | 0.50 |
| I | − | + | − | + | 0.30 |
| J | − | − | + | + | 0.50 |
| K | − | − | + | + | 0.30 |

III. Sulfonation and working up

The sulfonation of the fatty acid lower alkyl esters and the working up of the acidic sulfonation product were carried out by a standard method:

In a 1-liter sulfonation reactor equipped with a heating and cooling jacket and a gas inlet pipe, 1 mol fatty acid ester were heated to 80° C. and reacted with 9.6 g (1.2 mol) gaseous sulfur trioxide corresponding to a molar ratio of 1:1.2. The $SO_3$ had been driven out by heating from a corresponding quantity of 65% by weight oleum, diluted with nitrogen to a concentration of 5% by volume and introduced into the ester over a period of 60 minutes. The temperature of the reaction mixture was kept below 90° C.

After sulfonation, the crude sulfonation product was first subjected to an after-reaction for 15 minutes at 80° C. in a water bath and was then neutralized by stirring into a 25% by weight aqueous sodium hydroxide solution.

Before determination of the Klett color value, the α-sulfofatty acid lower alkyl ester salt was bleached for 120 minutes at 60° C. after addition of 2% by weight sodium hypochlorite, based on the content of washing-active substance.

The Klett color value of the products was determined with a Klett-Summerson model 800-3 Klett photometer (1 cm round cuvette, blue filter 400–465 nm) at a concentration of washing-active substance of 5% by weight and at pH 7.

The contents of oxo compounds and unsaturated compounds obtained after the pretreatment of esters I to III and the Klett color values of the resulting ester sulfonates are shown in Table 3 (Examples according to the invention) and Table 4 (Comparison Examples). The results represent the averages of 5 measurements.

TABLE 3

Contents of oxo compounds and unsaturated compounds and Klett color values (Examples according to the invention)

| Ex. | Process | Ester | Oxo compounds % by wt. | Unsat. compounds % by wt. | Klett Color values |
|---|---|---|---|---|---|
| 1.1 | A | I | 0.07 | 0.09 | 23 |
| 1.2 | B | I | 0.07 | 0.05 | 12 |
| 1.3 | C | I | 0.06 | 0.05 | 10 |
| 1.4 | D | I | 0.06 | 0.05 | 9 |
| 2.1 | A | II | 0.09 | 0.09 | 29 |
| 2.2 | B | II | 0.09 | 0.05 | 19 |
| 2.3 | C | II | 0.08 | 0.05 | 14 |
| 2.4 | D | II | 0.08 | 0.05 | 12 |
| 3.1 | A | III | 0.06 | 0.09 | 17 |
| 3.2 | B | III | 0.06 | 0.05 | 10 |
| 3.3 | C | III | 0.05 | 0.05 | 8 |
| 3.4 | D | III | 0.05 | 0.05 | 6 |

TABLE 4

Contents of oxo compounds and unsaturated compounds and Klett color values (Comparison Examples)

| Ex. | Process | Ester | Oxo compounds % by wt. | Unsat. compounds % by wt. | Klett Color values |
|---|---|---|---|---|---|
| C1.1 | E | I | 0.12 | 0.50 | 72 |
| C1.2 | F | I | 0.12 | 0.11 | 35 |
| C1.3 | G | I | 0.12 | 0.05 | 31 |
| C1.4 | H | I | 0.07 | 0.51 | 61 |
| C1.5 | I | I | 0.07 | 0.29 | 41 |
| C1.6 | J | I | 0.06 | 0.50 | 57 |
| C1.7 | K | I | 0.07 | 0.31 | 44 |
| C2.1 | E | II | 0.25 | 0.49 | 98 |
| C2.2 | F | II | 0.25 | 0.12 | 44 |
| C2.3 | G | II | 0.25 | 0.05 | 36 |
| C2.4 | H | II | 0.09 | 0.52 | 85 |
| C2.5 | I | II | 0.09 | 0.33 | 51 |
| C2.6 | J | II | 0.08 | 0.50 | 69 |
| C2.7 | K | II | 0.08 | 0.31 | 46 |

The content of oxo compounds and unsaturated compounds was determined by gas chromatography.

What is claimed is:
1. A process for the production of fatty acid lower alkyl esters for use in the production of light colored washing-active α-sulfofatty acid lower alkyl ester salts comprising the steps of

A) reducing the quantity of oxo compounds in a fatty acid lower alkyl ester to less than about 0.1% by weight by either or both of
   a) distilling the fatty acid lower alkyl ester in the presence of an inorganic acid or a partial glycerol ester of said inorganic acid, and/or
   b) by adsorption onto an inorganic solid selected from the group consisting of aluminum oxide, titanium dioxide, magnesium oxide, and silica gel; and
B) hydrogenating the fatty acid lower alkyl ester to reduce the content of unsaturated compounds to less than about 0.1% by weight;
wherein steps A) and B) are optionally carried out in reverse order.

2. The process of claim 1 where steps A) and B) are carried out in the order shown.

3. The process of claim 1 wherein in step A) a) the inorganic acid is phosphoric acid, hypophosphorus acid, or boric acid, and is used in a concentration of from about 0.05 to about 0.5% by weight of the fatty acid lower alkyl ester; in step A) b) the inorganic solid has a particle size of from about 0.03 to about 0.3 mm and is used in a concentration of from about 10 to about 150% by weight of the fatty acid lower alkyl ester; and step B) is carried out over a nickel catalyst at a temperature of from about 150° C. to about 220° C. and at a pressure of from about 5 to about 50 bar.

4. The process of claim 3 wherein the fatty acid lower alkyl ester is a $C_{6-22}$ fatty acid esterified with a $C_{1-4}$ alcohol.

5. A process for the production of a light colored washing-active α-sulfofatty acid lower alkyl ester salt which comprises the steps of
A) reducing the quantity of oxo compounds in a fatty acid lower alkyl ester to less than about 0.1% by weight by either or both of
   a) distilling the fatty acid lower alkyl ester in the presence of an inorganic acid or a partial glycerol ester of said inorganic acid, and/or
   b) by adsorption onto an inorganic solid selected from the group consisting of aluminum oxide, titanium dioxide, magnesium oxide, and silica gel;
B) hydrogenating the fatty acid lower alkyl ester to reduce the content of unsaturated compounds to less than about 0.1% by weight;
C) contacting the fatty acid lower alkyl ester with gaseous sulfur trioxide; and
D) neutralizing and bleaching the product from step C) to produce light colored washing-active α-sulfofatty acid lower alkyl ester salts;
wherein steps A) and B) are optionally carried out in reverse order.

6. The process of claim 5 wherein steps A) and B) are carried out in the order shown.

7. The process of claim 5 wherein in step A) a) the inorganic acid is phosphoric acid, hypophosphorous acid, or boric acid, and is used in a concentration of from about 0.05 to about 0.5% by weight of the fatty acid lower alkyl ester; in step A) b) the inorganic solid has a particle size of from about 0.03 to about 0.3 mm and is used in a concentration of from about 10 to about 150% by weight of the fatty acid lower alkyl ester; and step B) is carried out over a nickel catalyst at a temperature of from about 150° C. to about 220° C. and at a pressure of from about 5 to about 50 bar.

8. The process of claim 7 wherein the fatty acid lower alkyl ester is a $C_{6-22}$ fatty acid esterified with a $C_{1-4}$ alcohol.

9. The process of claim 5 wherein in step A) a) said inorganic acid is used in a concentration of from about 0.05 to about 0.5% by weight of said fatty acid lower about 0.05 to about 0.5% by weight of said fatty acid lower alkyl ester.

10. The process of claim 5 wherein in step A) a) said inorganic acid is phosphoric acid, hypophosphorous acid, or boric acid.

11. The process of claim 5 wherein in step A) a) said partial glycerol ester is an ester of phosphoric acid, hypophosphorous acid, or boric acid.

12. The process of claim 5 wherein in step A) b) said inorganic solid is used at a concentration of from about 10 to about 150% by weight of said fatty acid lower alkyl ester.

13. The process of claim 12 wherein said concentration is from about 25 to about 100% by weight of said fatty acid lower alkyl ester.

14. The process of claim 5 wherein in step A) b) the particle size of said inorganic solid is from about 0.03 to about 0.3 mm.

15. The process of claim 14 wherein said particle size of said inorganic solid is from about 0.06 to about 0.2 mm.

16. The process of claim 5 wherein step B) is carried out by hydrogenation over a nickel catalyst at a temperature of from about 150° C. to about 220° C. and at a pressure of from about 5 to about 50 bar.

17. The process of claim 16 wherein said temperature is from about 170° C. to about 190° C. and the pressure is from about 15 to about 25 bar.

18. The process of claim 5 wherein said fatty acid lower alkyl ester is a $C_{6-22}$ fatty acid esterified with a $C_{1-4}$ alcohol.

19. The process of claim 18 wherein said ester is a methyl ester of a $C_{8-18}$ fatty acid.

20. The process of claim 5 wherein said fatty acid lower alkyl ester is produced by the rolling-up process and subsequent esterification with methanol.

* * * * *